United States Patent
Brunn et al.

(10) Patent No.: US 11,389,384 B2
(45) Date of Patent: Jul. 19, 2022

(54) METHOD FOR PRODUCING A LIGHT-COLOURED DISALT

(71) Applicant: BASF SE, Ludwigshafen (DE)

(72) Inventors: Claudia Brunn, Düsseldorf-Holthausen (DE); Ansgar Behler, Düsseldorf-Holthausen (DE); Rainer Eskuchen, Düsseldorf-Holthausen (DE); Hans-Christian Raths, Düsseldorf-Holthausen (DE); Tobias Hoefener, Düsseldorf-Holthausen (DE)

(73) Assignee: BASF SE, Ludwigshafen (DE)

( * ) Notice: Subject to any disclaimer, the term of this patent is extended or adjusted under 35 U.S.C. 154(b) by 21 days.

(21) Appl. No.: 16/616,524

(22) PCT Filed: May 22, 2018

(86) PCT No.: PCT/EP2018/063288
§ 371 (c)(1),
(2) Date: Nov. 25, 2019

(87) PCT Pub. No.: WO2018/219705
PCT Pub. Date: Dec. 6, 2018

(65) Prior Publication Data
US 2020/0100998 A1    Apr. 2, 2020

(30) Foreign Application Priority Data

May 29, 2017   (EP) ..................................... 17173256

(51) Int. Cl.
| | |
|---|---|
| *A61K 8/46* | (2006.01) |
| *A61Q 5/02* | (2006.01) |
| *A61Q 9/02* | (2006.01) |
| *A61Q 11/00* | (2006.01) |
| *A61Q 19/10* | (2006.01) |
| *C11D 1/28* | (2006.01) |

(52) U.S. Cl.
CPC ............... *A61K 8/466* (2013.01); *A61Q 5/02* (2013.01); *A61Q 9/02* (2013.01); *A61Q 11/00* (2013.01); *A61Q 19/10* (2013.01); *C11D 1/28* (2013.01)

(58) Field of Classification Search
CPC .... C07C 143/16; C07C 309/17; C07C 303/44
USPC ........................................... 554/96, 98, 100
See application file for complete search history.

(56) References Cited

U.S. PATENT DOCUMENTS

| | | | | |
|---|---|---|---|---|
| 3,142,691 A | * | 7/1964 | Wulff | .................... C07C 309/17 554/96 |
| 4,252,796 A | * | 2/1981 | Yu | ............................ A61K 8/06 514/178 |
| 4,547,318 A | | 10/1985 | Kloetzer et al. | |

FOREIGN PATENT DOCUMENTS

| | | | | |
|---|---|---|---|---|
| CA | 1065888 | * | 11/1979 | .......... C07C 143/16 |
| DE | 1179931 B | | 10/1964 | |
| DE | 1234709 B | | 2/1967 | |
| DE | 3319591 A1 | | 12/1984 | |
| DE | 4203797 A1 | | 8/1993 | |
| DE | 4224735 A1 | | 2/1994 | |
| DE | 4235139 A1 | | 4/1994 | |
| WO | WO-2016/030172 A1 | | 3/2016 | |
| WO | WO2016030172 | * | 3/2016 | ............... A61K 8/44 |

OTHER PUBLICATIONS

International Application No. PCT/EP2018/063288, International Search Report, dated Jul. 19, 2018.

* cited by examiner

*Primary Examiner* — Walter E Webb
(74) *Attorney, Agent, or Firm* — Marshall, Gerstein & Borun LLP

(57) ABSTRACT

A process for preparing light-colored aqueous surfactant compositions containing 10% by weight to 60% by weight, based on the total composition, of one or more alpha-sulfo fatty acid disalts (A) of general formula (I), $$R^1CH(SO_3M^1)COOM^2 \quad (I),$$

in which radical $R^1$ is a linear or branched alkyl or alkenyl radical having 6 to 18 carbon atoms and radicals $M^1$ and $M^2$, independently, are selected from the group comprising H, Li, Na, K, Ca/2, Mg/2, ammonium, and alkanolamines, and water,
in which fatty acids of the general formula (Ia), $$R^2CH_2COOH \quad (Ia)$$

in which radical $R^2$ is a linear or branched alkyl or alkenyl radical having 6 to 18 carbon atoms,
(i) are subjected to sulfonation with gaseous sulfur trioxide,
(ii) the acidic sulfonation product is neutralized, and then
(iii) is subjected to bleaching with hydrogen peroxide at a pH above 7 in a temperature range of 80 to 95° C. in the presence of 50 to 500 ppm, based on the total composition of a stabilizer selected from the group comprising magnesium oxide, magnesium salts, water glass, nitrilotriacetic acid, ethylenediaminetetraacetic acid, gluconic acid, and salts thereof.

12 Claims, No Drawings

METHOD FOR PRODUCING A LIGHT-COLOURED DISALT

CROSS-REFERENCE TO RELATED APPLICATIONS

This application is the U.S. National Stage application of International Patent Application No. PCT/EP2018/063288, filed May 22, 2018, which claims the benefit of European Patent Application No. 17173256.3, filed May 29, 2017.

FIELD OF THE INVENTION

The present invention relates to a process for preparing light-colored aqueous surfactant compositions with a content of alpha-sulfo fatty acid disalts.

STATE OF THE ART

Anionic surfactants are some of the most widespread interface-active compounds and, apart from being used in detergents and cleaners, are also used for diverse purposes in the field of cosmetics. Customary anionic surfactants as are used in particular in cosmetics are the salts of alkyl ether sulfates (alkyl polyether sulfates, fatty alcohol polyglycol ether sulfates, in short also ether sulfates). They are characterized by a strong foaming ability, high cleaning power, low sensitivity to hardness and grease and are used widely for producing cosmetic products such as, for example, hair shampoos, foam or shower baths, but also in hand dishwashing detergents.

For many current applications, apart from a good interface-active effect, further requirements are placed on anionic surfactants. A high dermatological compatibility is required in particular in cosmetics. In addition, good foaming ability and a pleasant sensory feel to the foam are generally desired. Furthermore, there is a need for anionic surfactants which can be produced at least partially from biogenic sources and specifically also renewable raw materials. Surfactants which meet this requirement perfectly are alpha-sulfo fatty acid disalts, such as are accessible, for example, by sulfonation of fatty acids with gaseous sulfur trioxide together with subsequent neutralization.

The sulfonation of saturated fatty acids for preparing alpha-sulfo fatty acids is long known from the literature. The sulfonation is typically effected by reacting fatty acids with gaseous sulfur trioxide. The products obtainable in this case, however, are dark-colored and in this form are of only limited use.

Various patent documents are concerned with optimization of the sulfonation conditions in order to reduce as far as possible from the outset the primary formation of color carriers, compare, for example, DE 4224735 and documents cited therein. The improvement of the primary color alone, however, does not result in an acceptable product color. In this manner, only more bleachable products can be provided. A post-treatment in the form of bleach is nevertheless always required.

It is known that bleaching of sulfonated products of fatty acid esters can be carried out with hydrogen peroxide, wherein the bleaching is carried out fully or partially with the not yet neutralized, acidic crude sulfonic acid (compare, for example, DE 1179931, DE1234709, DE3319591). Investigations by the applicant, however, have shown that this is not easily transferable to the bleaching of sulfonation products of fatty acids since, when bleaching non-neutralized acidic sulfonation products of fatty acids, gelling occurs.

Investigations by the applicant have also shown that bleaching of neutralized aqueous pastes of sulfonation products of fatty acids, which is carried out using hydrogen peroxide at a pH of 7 or less, does not achieve acceptable product colors. An acceptable product color requires the use of very large amounts of hydrogen peroxide, a long process time, and also complex process monitoring and control, especially to avoid uncontrollable foam formation, and also results in undesirable dilution, that is to say water ingress.

DESCRIPTION OF THE INVENTION

The object of the present invention consisted of providing a simple, reliable, reproducible and economically viable process for preparing light-colored aqueous surfactant compositions comprising alpha-sulfo fatty acid disalts, based on sulfonation of fatty acids with gaseous sulfur trioxide together with subsequent neutralization and bleaching, but which solves the technical problems of hydrogen peroxide bleaching mentioned above.

In the context of the present invention, the term "light-colored" is understood to mean that the aqueous surfactant compositions, after dilution to a dry residue of 4% by weight—based on the total content of the diluted solution—have a Hazen color number of 200 Hazen or less, preferably 100 Hazen or less. The dilution for the color measurement in this case is effected with a mixture of deionized water (95% by weight) and isopropanol (5% by weight). The color measurement is conducted in an 11 mm round cuvette in a commercially available color measurement instrument (e.g. Lico 500 from Hach Lange GmbH).

The invention relates to a process for preparing light-colored aqueous surfactant compositions comprising 10% by weight to 60% by weight—based on the total composition—of one or more alpha-sulfo fatty acid disalts (A) of the general formula (I), $$R^1CH(SO_3M^1)COOM^2 \qquad (I),$$

in which the radical $R^1$ is a linear or branched alkyl or alkenyl radical having 6 to 18 carbon atoms and the radicals $M^1$ and $M^2$—independently of one another—are selected from the group comprising H, Li, Na, K, Ca/2, Mg/2, ammonium and alkanolamines, water, wherein the process is characterized in that fatty acids of the general formula (Ia), $$R^2CH_2COOH \qquad (Ia)$$

in which the radical $R^2$ is a linear or branched alkyl or alkenyl radical having 6 to 18 carbon atoms, (i) are subjected to sulfonation with gaseous sulfur trioxide,
(ii) the acidic sulfonation product—optionally after aging—is neutralized and then
(iii) is subjected to bleaching with hydrogen peroxide, wherein the bleaching is carried out at a pH above 7 in a temperature range of 80 to 95° C. in the presence of 50 to 500 ppm—based on the total composition—of a stabilizer selected from the group comprising magnesium oxide, magnesium salts, water glass, nitrilotriacetic acid, ethylenediaminetetraacetic acid, gluconic acid and salts thereof.

As detailed above, the compositions obtained by the process according to the invention comprise 10% by weight to 60% by weight—based on the total composition—of one or more alpha-sulfo fatty acid disalts (A) of the general formula (I). In a preferred embodiment, the compositions comprise 30% by weight to 40% by weight—based on the total composition—of one or more alpha-sulfo fatty acid disalts (A) of the general formula (I).

In formula (I), the radicals $M^1$ and $M^2$ are preferably sodium (Na).

As detailed above, the process according to the invention entails that firstly fatty acids are reacted with gaseous sulfur trioxide. In this case, the sulfur trioxide is preferably used in an amount, in that the molar ratio of $SO_3$ to fatty acids is in the range from 1.0:1.0 to 1.5:1.0. The fatty acids are introduced in this case into the reactor at a reservoir temperature in the range of 70 to 95° C. Preferably, the liquid sulfonation product obtained after the sulfonation is maintained and aged at this temperature for 5 to 20 minutes in a temperature-controlled postreaction coil.

The crude products obtained in this way, which are acidic sulfonation products, are then partially or completely neutralized, preference being given to complete neutralization with aqueous NaOH.

For the subsequent bleaching with hydrogen peroxide, the conditions specified above apply, i.e.
1. The pH is above 7.
2. The temperature is in the range from 80 to 95° C.
3. The bleaching takes place in the presence of 50 to 500 ppm—based on the total composition—of a stabilizer selected from the group comprising magnesium oxide, magnesium salts, water glass, nitrilotriacetic acid, ethylenediaminetetraacetic acid, gluconic acid and salts thereof.

Preferably, the aqueous surfactant composition to be bleached is initially charged in a reactor, stirred and temperature-controlled, and adjusted to the desired pH. To the aqueous surfactant composition is then firstly added a stabilizer which, under the bleaching conditions selected, prevents a sudden decomposition of the hydrogen peroxide and thus uncontrollable foam formation and release of heat. The stabilizer is preferably used in an amount of 200 to 400 ppm—based on the total composition.

The initial charge thus prepared is treated with hydrogen peroxide ($H_2O_2$). The hydrogen peroxide is preferably used here as an aqueous solution at a commercially available concentration of 30%-70% by weight, preferably 30%-45% by weight. The metered addition of the hydrogen peroxide into the initially charged surfactant composition is carried out continuously, preferably via a tube submerged below the liquid level. The metering rate is particularly selected such that a steady-state peroxide concentration of <3000 ppm, preferably 100 to 1000 ppm is set, whereby a constant bleaching progression is ensured.

The bleaching is preferably effected at a temperature in the range of 85 to 92° C. The pH of the aqueous solution during the bleaching is adjusted particularly to a value in the range of 10-11.5 and especially 10.2 to 10.7. In the case of a drop in the pH during the course of the bleaching process, this is readjusted. The pH is adjusted with aqueous NaOH. In this case, the concentration of the NaOH solution used is at most 50% by weight, preferably at most 20% by weight.

Use of the Compositions

A further subject matter of the invention is the use of the surfactant compositions obtainable by the process according to the invention for cosmetic compositions, and also detergents and cleaners.

With regard to cosmetic products, particular preference is given here especially to those which are present in the form of hair shampoos, shower gels, soaps, syndets, washing pastes, washing lotions, scrub preparations, foam baths, oil baths, shower baths, shaving foams, shaving lotions, shaving creams and dental care products (for example toothpastes, mouthwashes and the like).

With regard to cleaners, of preference here are in particular products with a low pH for cleaning hard surfaces, such as bath and WC cleaners and the like, and also for cleaning and/or fragrance gels for use in sanitary installations.

Examples

Substances Used
Starting Material Used:
unbleached, aqueous composition comprising an alpha-sulfo fatty acid disodium salt of technical grade quality based on native $C_{12/14}$-fatty acid ($C_{12/14}$ weight ratio 70:30); composition: water content 46.5%, dry residue 53.5% consisting of alpha-sulfo fatty acid or (di)sodium salt, $C_{12/14}$-fatty acid or sodium salt and sodium sulfate approximately in the ratio 8:1:1, pH 5.1.

The color of this composition was measurable using the method specified below only after further dilution by a factor of 10 (corresponds to 0.4% by weight dry residue) and was then at 330 Hazen.

Measurement Methods Used
pH: Using a standard commercial pH meter, the pH was measured directly in the formulation, i.e. the aqueous surfactant composition.
Color: The aqueous surfactant compositions were diluted with a mixture of deionized water (95% by weight) and isopropanol (5% by weight) to a dry residue of 4% by weight—based on the total content of the diluted solution. The color value of this solution was determined in an 11 mm round cuvette in a commercial color measuring instrument from Hach Lange GmbH (Lico 500). The color value is stated in Hazen units.
Peroxide concentration: The peroxide concentration was determined by means of semiquantitative test strips (MQuant from Merck) adjusted in aqueous dilution to the measuring range of the test strips.

Results of the Bleaching Experiments
The data in Table 1 and 2 are based in each case on an initial charge amount of 100 kg.

TABLE 1

| Bleaching conditions | Example 1 | Comparative example 1 | Comparative example 2 |
| --- | --- | --- | --- |
| Temperature | 90° C. | 90° C. | 90° C. |
| pH | 10.4-10.7 | 5.3-6.6 | 10.4 |
| Stabilizer | Magnesium oxide 300 ppm | — | — |
| Bleaching agent, total amount used | Hydrogen peroxide (35%) 5.1 kg | Hydrogen peroxide (35%) 2.26 kg | Hydrogen peroxide (35%) <0.5 kg |

TABLE 1-continued

| Bleaching conditions | Example 1 | Comparative example 1 | Comparative example 2 |
|---|---|---|---|
| Steady-state peroxide concentration | 100-300 ppm | 1000-1500 ppm | — |
| pH modifier, total amount used | NaOH (20%), 16.8 kg | NaOH (50%), 6.83 kg | NaOH (20%), 12.0 kg |
| Finished color and bleaching duration | 88 Hazen after 18 h, Termination since desired color attained | 399 Hazen after 30 h, Termination due to longer duration | — |
| Tendency to foam during the bleaching process | low | severe | extremely severe Termination necessary |

In inventive Example 1, the process conditions were selected such that good, controlled bleaching progress was ensured (see decrease of the product color over process duration, compare Table 2). After 18 hours, a very light-colored product (88 Hazen) was obtained.

In comparative example 1, conditions were selected which are obvious to those skilled in the art from the prior art. It was shown that in a pH range below 7, i.e. in the acidic pH range, even at a relatively high steady-state peroxide concentration, no acceptable bleaching progress can be achieved (see decrease of the product color with process duration, compare Table 2). After 30 hours, the product was still too dark. The experiment was then terminated due to the long process duration. In addition, the resulting foam formation proved to be problematic.

Comparative example 2 shows that, without addition of a stabilizer, bleaching in the alkaline pH range could not be started at all. Peroxide metered in decomposed immediately with extremely severe foam formation.

Table 2 below shows the product color measured as a function of time during the bleaching process. The first-mentioned Hazen value in each case in Example 1 and comparative example 1 is that which is in the measurable range.

TABLE 2

| Bleaching time | Example 1 Color (in Hazen) | Comparative example 1 Color (in Hazen) |
|---|---|---|
| After 5 hours | 850 | |
| After 6 hours | 480 | |
| After 8 hours | 300 | |
| After 10 hours | 220 | |
| After 13 hours | 170 | |
| After 15 hours | 120 | |
| After 17 hours | 100 | 831 |
| After 18 hours | 88 | |
| After 20 hours | | 723 |
| After 23 hours | | 597 |
| After 28 hours | | 480 |
| After 30 hours | | 399 |

The invention claimed is:

1. A process for preparing a light-colored aqueous surfactant composition comprising
    10% by weight to 60% by weight, based on the total composition, of one or more alpha-sulfo fatty acid disalt (A) of a general formula (I),

    $$R^1CH(SO_3M^1)COOM^2 \quad (I)$$

in which radical $R^1$ is a linear or branched alkyl or alkenyl radical having 6 to 18 carbon atoms and the radicals $M^1$ and $M^2$, independently of one another, are selected from the group consisting of H, Li, Na, K, Ca/2, Mg/2, ammonium, and alkanolamine,
    water,
    wherein a fatty acid of a general formula (Ia),

    $$R^2CH_2COOH \quad (Ia)$$

in which the radical $R^2$ is a linear or branched alkyl or alkenyl radical having 6 to 18 carbon atoms,
    (i) is subjected to sulfonation with gaseous sulfur trioxide,
    (ii) the acidic sulfonation product, optionally after aging, is neutralized, and then
    (iii) is subjected to bleaching with hydrogen peroxide, wherein the bleaching is carried out at a pH above 7 in a temperature range of 80 to 95° C. in a presence of 50 to 500 ppm, based on the total composition, of a stabilizer selected from the group consisting of magnesium oxide, magnesium salts, water glass, nitrilotriacetic acid, ethylenediaminetetraacetic acid, gluconic acid, and salts thereof.

2. The process according to claim 1, wherein the radical $R^1$ in the formula (I) is a saturated, linear alkyl radical having 10 to 16 carbon atoms, where with regard to the compound (A) it is the case that a fraction of the compound (A) in which the radical $R^1$ is a decyl or a dodecyl radical, based on the total amount of the compound (A), is 90% by weight or more.

3. The process according to claim 1, wherein the radicals $M^1$ and $M^2$ are sodium.

4. The process according to claim 1, wherein magnesium oxide is used as stabilizer in the bleaching step (iii).

5. The process according to claim 1, wherein the stabilizer in the bleaching step (iii) is used in an amount of 200 to 400 ppm.

6. The process according to claim 1, wherein in the bleaching step (iii), the temperature in the bleaching step (iii) is adjusted in the range from 85 to 92° C.

7. The process according to claim 1, wherein in the bleaching step (iii), the pH is adjusted to a value in the range from 10-11.5.

8. The process according to claim 1, wherein in the bleaching step (iii), the pH is adjusted to a value in the range from 10.2 to 10.7.

9. The process according to claim 1, wherein in the bleaching step (iii), hydrogen peroxide in the form of an aqueous solution is used at a commercially available concentration of 30 to 70% by weight.

10. The process according to claim 1, wherein in the bleaching step (iii), the hydrogen peroxide is metered in continuously below the liquid level into the initially charged surfactant composition.

11. The process according to claim 10, wherein in the bleaching step (iii), a metered addition rate of the hydrogen peroxide is selected such that a stationary peroxide concentration is set which is below 3000 ppm.

12. The process according to claim 10, wherein in the bleaching step (iii), a metered addition rate of the hydrogen peroxide is selected such that a stationary peroxide concentration is set which is in the range of 100 to 1000 ppm.

\* \* \* \* \*